United States Patent [19]

Pastor et al.

[11] Patent Number: 5,326,802
[45] Date of Patent: Jul. 5, 1994

[54] BETA CRYSTALLINE MODIFICATION OF 2,2',2''-NITRILO[TRIETHYL-TRIS-(3,3',5,5'-TETRA-TERT-BUYTL-1,1'-BIPHENYL-2,2'-DIYL)PHOSPHITE]

[75] Inventors: Stephen D. Pastor, Danbury, Conn.; Sai P. Shum, Hawthorne, N.Y.

[73] Assignee: Ciba-Geigy Corporation, Ardsley, N.Y.

[21] Appl. No.: 983,181

[22] Filed: Nov. 30, 1992

[51] Int. Cl.$^5$ .................. C07F 9/6574; C08K 5/52
[52] U.S. Cl. ......................... 524/119; 558/78; 558/147
[58] Field of Search ............... 558/78, 147; 524/119

[56] References Cited

U.S. PATENT DOCUMENTS 4,318,845 3/1982 Spivack et al. .
4,374,219 2/1983 Spivack et al. .
4,683,326 7/1987 Orban et al. .

OTHER PUBLICATIONS

Pure & Appl. Chem. vol. 45, pp. 1-1–30 Pergamon Press 1976.

*Primary Examiner*—Veronica P. Hoke
*Attorney, Agent, or Firm*—Luther A. R. Hall

[57] ABSTRACT

The beta crystalline modification of 2,2',2''-nitrilo[triethyl-tris-(3,3',5,5'-tetra-tertbutyl-1,1'-biphenyl-2,2'-diyl) phosphite] is obtained by crystallizing said compound from the melt at elevated temperatures.

The beta crystalline form is an effective process stabilizer for polyolefins, particularly polypropylene.

8 Claims, No Drawings

BETA CRYSTALLINE MODIFICATION OF 2,2',2"-NITRILO[TRIETHYL-TRIS-(3,3',5,5'-TETRA-TERT-BUYTL-1,1'-BIPHENYL-2,2'-DIYL)PHOSPHITE]

This invention pertains to a novel crystalline modification of 2,2',2"-nitrilo[triethyl-tris-(3,3',5,5'tetra-tert-butyl-1,1'-biphenyl-2,2'-diyl) phosphite] and to processes for preparing said modification.

BACKGROUND OF THE INVENTION 2,2',2"-Nitrilo[triethyl-tris-(3,3',5,5'-tetra-tert-butyl-1,1'-biphenyl-2,2'-diyl) phosphite] is a compound having the formula I

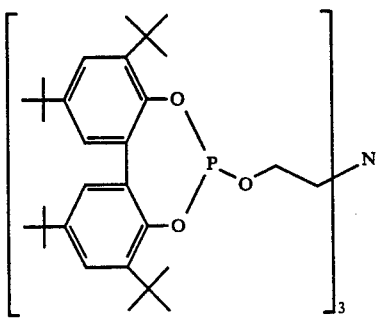

This compound of formula I is useful as a processing stabilizer for organic polymers as taught in U.S. Pat. Nos. 4,318,845 and 4,374,219. The compound of formula I is disclosed as being a white powder melting at 121°-134° C. As such, the powdery product has defects in terms of handling and apparent density, exhibiting poor flowability, meterability, storage stability and hydrolytic stability.

It has now been found that the compound of formula I can be obtained in a different crystalline modification as purified crystalline particles which exhibit acceptable properties in respect to handling, apparent density, flowability, meterability, storage stability and hydrolytic stability.

The new modification is characterized by a triclinic crystalline form, melting in the range of 200°-207° C. as given by the peak temperature of the endotherm recorded by differential scanning calorimetry (DSC); and by an X-ray diffraction pattern obtained using Cu-Kα which exhibits diffraction angles (2Θ) of very high intensity at 8.4 and 17; lines of high intensity at 9.9, 10.6, 11.4, 17.5, 19.1, 20.2; lines of medium intensity at 4.6, 4.9, 7.1, 12.7, 13.2, 13.6, 15.3, 15.8, 16.4, 16.7, 18.4, 19.7, 21.7, 23.4; and lines of weak intensity at 7.8, 8.8, 9.4, 12, 14.1, 14.6, 21, 22.3, 22.8, 23.9, 24.7, 25.3, 25.5, 26.4, 27.27.7, 28.4 and a relative absolute configuration of the three stereo axes of the dibenzo[d,f][1,3,2]dioxaphosphepin rings of R*,R*,S*.

R* and S* follow the customary convention when the absolute configuration of a molecule is unknown. The nomenclature adopted here is based on recent Chemical Abstracts Service practice as described by L. C. Cross and W. Kylne, Pure Appl. Chem. 45, 11-30 (1976).

The instant invention also relates to processes for the preparation of this novel beta crystalline modification of the compound of formula I.

The instant invention also pertains to a composition stabilized against thermal, oxidative and actinic induced degradation which comprises
 (a) a polyolefin, and
 (b) an effective amount of the beta crystalline form of 2,2',2"-nitrilo[triethyl-tris-(3,3',5,5'-tetra-tert-butyl-1,1'-biphenyl-2,2'-diyl)phosphite], characterized by melting in the range of 200°-207° C. and by an X-ray diffraction pattern exhibiting lines of very high intensity at 8.4 and 17; lines of high intensity at 9.9, 10.6, 11.4, 17.5, 19.1, 20.2; lines of medium intensity at 4.6, 4.9, 7.1, 12.7, 13.2, 13.6, 15.3, 15.8, 16.4, 16.7, 18.4, 19.7, 21.7, 23.4; and lines of weak intensity at 7.8, 8.8, 9.4, 12, 14.1, 14.6, 21, 22.3, 22.8, 23.9, 24.7, 25.3, 25.5, 26.4, 27.27.7 , 28.4 and a relative absolute configuration of the stereo axes of the dibenzo[d,f][1,3,2]dioxaphosphepin rings of R*,R*,S*.

Preferably, the polyolefin is polypropylene.

One process for the preparation of the instant beta crystalline modification comprises heating a melt of the compound of formula I at a temperature in the range of 170° to 200° C. until the novel beta crystalline modification forms or optionally seed the melt with the novel beta crystalline form in order to increase the rate and efficiency of the melt crystallization. The melt crystallization is optionally carried out under reduced pressure of from 400 mm Hg to 0.1 mm Hg. The melt crystallization can also be carried out in an extruder or kneader as described in U.S. Pat. No. 4,683,326, the relevant parts of which are herein incorporated by reference.

An alternative process for the preparation of the beta crystalline modification of the compound of formula I is crystallizing or recrystallizing the compound of formula I from a mixture of an aromatic hydrocarbon solvent and an alcohol of 4 to 8 carbon atoms; from a mixture of an aliphatic ketone and an alcohol of 1 to 8 carbon atoms; or from a mixture of an aromatic hydrocarbon solvent and an aliphatic ketone.

Examples of aromatic hydrocarbon solvents useful in the instant process are benzene, toluene, o-xylene, m-xylene, p-xylene, 1,2,3-trimethylbenzene, 1,3,5-trimethylbenzene, 1,2,4-trimethylbenzene, 1,2,4,5-tetramethylbenzene, ethylbenzene, cumene, o-cymene, m-cymene, p-cymene, o-diisopropylbenzene, m-diisopropylbenzene, p-diisopropylbenzene, and mixtures of such aromatic hydrocarbon solvents.

Examples of alcohols useful in the instant process are methanol, ethanol, 1-propanol, isopropanol, 1-butanol, 2-butanol, tert-butyl alcohol, isobutanol, amyl alcohol, 1-hexanol, 2-ethylhexanol, 1-octanol and mixtures of such alkanols.

Examples of aliphatic ketones are acetone, 2-butanone, 2-pentanone, 3-pentanone, 2-heptanone and the like.

Differential scanning calorimetry (DSC) measurements are obtained on a TA Instrument Inc., 910 differential scanning calorimeter, with a 100 mL/min nitrogen purge, aligned aluminum pan, temperature scan at 5° C./min to 230° C.

X-ray diffraction patterns are recorded on a Philips Norelco X-ray Diffractometer unit, using Cu-Kα radiation with a nickel filter.

EXAMPLE 1

The compound of formula I, 2,2',2"-nitrilo[triethyl-tris-(3,3',5,5'-tetra-tert-butyl-1,1'-biphenyl-2,2'-diyl) phosphite], is prepared according to procedure of Example 4 of U.S. Pat. No. 4,318,845. The product obtained is heated at 180°-185° C. in vacuo (0.1 mm Hg) to obtain a melt. The melt is heated until a crystalline mass forms, approximately 16 hours. The crystalline mass is then ground into a white powder using a mortar and pestle. A 93% yield of the novel beta crystal modification of the compound of formula I is obtained: m.p.=206° C. (the melting point is determined by differential scanning calorimetry and the peak temperature in the endotherm is recorded as the melting point).

An X-ray diffraction pattern obtained using Cu-Kα exhibits diffraction angles (2Θ) of very high intensity at 8.4 and 17; lines of high intensity at 9.9, 10.6, 11.4, 17.5, 19.1, 20.2; lines of medium intensity at 4.6, 4.9, 7.1, 12.7, 13.2, 13.6, 15.3, 15.8, 16.4, 16.7, 18.4, 19.7, 21.7, 23.4; and lines of weak intensity at 7.8, 8.8, 9.4, 12, 14.1, 14.6, 21, 22.3, 22.8, 23.9, 24.7, 25.3, 25.5, 26.4, 27.27.7, 28.4.

Analysis: Calcd for $C_{90}H_{132}NO_9P_3$: C, 73.8; H, 9.1; N, 0.96. Found: C, 73.5; H, 9.4; N, 0.9.

EXAMPLE 2

The compound of formula I is prepared according to the procedure of Example 4 of U.S. Pat. No. 4,318,845. The compound is recrystallized from the following solvent systems to obtain the novel beta crystalline modification of the instant invention.

| Solvent (wt/wt) | Compound/ Solvent Ratio (wt/wt) | mp (°C.)* | (%) Yield |
|---|---|---|---|
| toluene/ 1-butanol (1/1) | 1/8.4 | 205 | 93 |
| 1-butanol/ 2-butanone (2.3/1) | 1/8.1 | 206 | 55 |
| acetone/ toluene (3.6/1) | 1/8 | 206 | 66 |

*Melting point is determined by differential scanning calorimetry and the peak temperature in the endotherm is recorded as the melting point.

Suitable crystals for X-ray analysis are grown from acetone/toluene (3.6/1, wt/wt). Intensity data are measured on a NONIUS CAD4 automatic diffractometer as described in Table 1. The structure is solved by direct methods using SHELXS. Full-matrix least-squares refinements are carried out to a final R value of 0.083. The relative configuration is determined to be $R^*,R^*,S^*$.

TABLE 1

Crystal and Data Collection Parameter for Novel Crystal Modification

| Formula | $C_{90}H_{132}NO_9P_3$ |
|---|---|
| Formula weight (g · mol$^{-1}$) | 1464.96 |
| Color; Habit | Colorless Prism |
| Crystal System | Triclinic |
| Space group | PI |
| Z | 2 |
| Cell parameters | a = 12.493 (1) Å |
|  | b = 19.701 (2) Å |
|  | c = 21.027 (3) Å |
|  | α = 116.23 (1) deg |
|  | β = 100.15 (1) deg |
|  | γ = 91.07 (1) deg |
| Volume | ν = 4542 Å$^3$ |
| $d_{calc}$ | 1.072 g/cm$^3$ |
| Absorption Coefficient | 0.926 mm$^{-1}$ |
| Crystal Size | 0.5 × 0.3 × 0.2 mm |
| Temperature | 21 C. |
| Diffractometer Type | NONIUS CAD4 |
| Radiation | CuKα (λ = 1.5418 Å) |
| Monochromator | Orientated graphite crystal |
| 2θ Range | 3 to 50 deg |
| Reflections Collected | 14042 |
| R | 0.083 |
| $R_W$ | 0.090 |

EXAMPLE 3

Comparative Example

The compound of formula I, prepared according to the procedure of Example 4 of U.S. Pat. No. 4,318,845 and not recrystallized according to the procedures of this invention, is heated at 210° C. until a clear melt is obtained. The melt is cooled rapidly to ambient temperature to yield a glassy solid with a $T_g$ (DSC) of 105°–110° C. The X-ray diffraction pattern of this product obtained using Cu-Kα is featureless.

Analysis: Calcd for $C_{90}H_{132}NO_9P_3$: C, 73.8; H, 9.1; N, 0.96. Found: C, 73.4; H, 9.3; N, 0.9.

EXAMPLE 4

Resistance to Hydrolysis

This example illustrates the much greater resistance to hydrolysis of the beta crystalline modification of the compound of formula I as prepared in Example 1 as compared to the lesser resistance of the amorphous form of the compound of formula I as prepared in Example 3 and of the compound of Example 4 of U.S. Pat. No. 4,318,845.

The test compounds are exposed to 80% relative humidity at 50° C. and their rate of hydrolysis is monitored by liquid chromatography. The results below are stated in the percent product remaining after 1000 hours of exposure under the conditions stated above.

| Compound of | Percent Product Remaining After 1000 hours |
|---|---|
| Example 1 (beta crystalline form) | 85 |
| Example 3 (amorphous) | 50 |
| Example 4 of U.S. Pat. No. 4,318,845 (prior art) | 77 |

EXAMPLE 5

Bulk Density

This example illustrates the superior packaging properties of the novel beta crystalline modification of the compound of formula I, Example 1, over that of the powder form of Example 4 in U.S. Pat. No. 4,318,845.

The apparent bulk density of the solids is measured according to the method of ASTM D-1895 (79). A higher apparent bulk density allows for a greater mass per unit volume which affords advantages in packaging of the solid product, such as lower costs for the packaging material, less storage space is required, etc.

| Compound of | Bulk Density (g/mL) |
|---|---|
| Example 1 (beta crystalline form) | 0.58 |
| Example 4 of U.S. Pat. No. 4,318,845 (prior art) | 0.44 |

EXAMPLE 6

Process Stabilization of Propylene at 525° F. (274° C.)

When unstabilized polypropylene containing 0.075% by weight of calcium stearate is admixed with an effective amount of the beta crystalline form solid of Example 1 and then extruded from an extruder at 525° F. (274° C.), the melt flow rate (in grams/10 minutes) is determined by ASTM method D1238.

The instant beta crystalline form compound is particularly effective in stabilizing polypropylene against thermal and oxidative degradation as shown by a minimum change in the melt flow rate.

What is claimed is:

1. A process for the preparation of the beta, triclinic crystalline form of the compound 2,2′,2″-nitrilo[triethyl-tris-(3,3′,5,5′-tetra-tert-butyl-1,1′-biphenyl-2,2′-diyl)-phosphite], characterized by melting in the range of 200°–207° C. and by an X-ray diffraction pattern exhibiting lines of very high intensity at 8.4 and 17; lines of high intensity at 9.9, 10.6, 11.4, 17.5, 19.1, 20.2; lines of medium intensity at 4.6, 4.9, 7.1, 12.7, 13.2, 13.6, 15.3, 15.8, 16.4, 16.7, 18.4, 19.7, 21.7, 23.4; and lines of weak intensity at 7.8, 8.8, 9.4, 12, 14.1, 14.6, 21, 22.3, 22.8, 23.9, 24.7, 25.3, 25.5, 26.4, 27.27.7, 28.4 and a relative absolute configuration of the three stereo axes of the dibenzo[d,f][1,3,2]dioxaphosphepin rings of R*,R*,S*, which comprises heating a melt of the compound 2,2′,2″-nitrilo[triethyl-tris-(3,3′,5,5′-tetra-tert-butyl-1,1′-biphenyl-2,2′-diyl)phosphite] at a temperature in the range of 170° to 200° C. to crystallize the novel beta crystalline modification.

2. A process for the preparation of the beta, triclinic crystalline form of the compound 2,2′,2″-nitrilo[triethyl-tris-(3,3′,5,5′-tetra-tert-butyl-1,1′-biphenyl-2,2′-diyl)-phosphite], characterized by melting in the range of 200°–207° C. and by an X-ray diffraction pattern exhibiting lines of very high intensity at 8.4 and 17; lines of high intensity at 9.9, 10.6, 11.4, 17.5, 19.1, 20.2; lines of medium intensity at 4.6, 4.9, 7.1, 12.7, 13.2, 13.6, 15.3, 15.8, 16.4, 16.7, 18.4, 19.7, 21.7, 23.4; and lines of weak intensity at 7.8, 8.8, 9.4, 12, 14.1, 14.6, 21, 22.3, 22.8, 23.9, 24.7, 25.3, 25.5, 26.4, 27.27.7, 28.4 and a relative absolute configuration of the three stereo axes of the dibenzo[d,f][1,3,2]dioxaphosphepin rings of R*,R*,S*, which comprises crystallizing or recrystallizing said compound from a mixture of an aromatic hydrocarbon solvent and an alcohol of 4 to 8 carbon atoms; from a mixture of an aliphatic ketone and an alcohol; or from a mixture of an aromatic hydrocarbon solvent and an aliphatic ketone.

3. A process according to claim 1 which comprises seeding the melt with the novel beta crystalline form in order to increase the rate and efficiency of the melt crystallization.

4. A process according to claim 1 wherein the melt is heated under reduced pressure of from 400 mm Hg to 0.1 mm Hg.

5. A process according to claim 1 wherein the melt crystallization is carried out in an extruder or kneader.

6. The beta, triclinic crystalline form of 2,2′,2″-nitrilo[triethyl-tris-(3,3′,5,5′-tetra-tert-butyl-1,1′-biphenyl-2,2′-diyl)phosphite], characterized by melting in the range of 200°–207° C. and by an X-ray diffraction pattern exhibiting lines of very high intensity at 8.4 and 17; lines of high intensity at 9.9, 10.6, 11.4, 17.5, 19.1, 20.2; lines of medium intensity at 4.6, 4.9, 7.1, 12.7, 13.2, 13.6, 15.3, 15.8, 16.4, 16.7, 18.4, 19.7, 21.7, 23.4; and lines of weak intensity at 7.8, 8.8, 9.4, 12, 14.1, 14.6, 21, 22.3, 22.8, 23.9, 24.7, 25.3, 25.5, 26.4, 27.27.7, 28.4 and a relative absolute configuration of the three stereo axes of the dibenzo[d,f][1,3,2]dioxaphosphepin rings of R*,R*,S*.

7. A composition stabilized against thermal, oxidative and actinic induced degradation which comprises
(a) a polyolefin, and
(b) an effective amount of the beta crystalline form of 2,2′,2″-nitrilo[triethyl-tris-(3,3′,5,5′-tetra-tert-butyl-1,1′-biphenyl-2,2′-diyl)phosphite] according to claim 6.

8. A composition according to claim 7 wherein the polyolefin is polypropylene.

* * * * *